United States Patent [19]
Bakas et al.

[11] Patent Number: 4,826,801
[45] Date of Patent: May 2, 1989

[54] CATALYTIC COMPOSITION FOR THE ALKYLATION AND TRANSALKYLATION OF AROMATIC HYDROCARBONS

[75] Inventors: Steve T. Bakas, Willowbrook; Paul T. Barger, Arlington Heights, both of Ill.

[73] Assignee: UOP, Des Plaines, Ill.

[21] Appl. No.: 124,147

[22] Filed: Nov. 23, 1987

Related U.S. Application Data

[63] Continuation-in-part of Ser. No. 932,113, Nov. 18, 1986, Pat. No. 4,735,924, which is a continuation-in-part of Ser. No. 772,099, Sep. 3, 1985, abandoned.

[51] Int. Cl.[4] ............................................. B01J 29/18
[52] U.S. Cl. ........................................ 502/64; 502/78
[58] Field of Search ..................................... 502/64, 78

[56] References Cited

U.S. PATENT DOCUMENTS 3,551,510 12/1970 Pollitzer et al. .................... 260/672
4,735,929 4/1988 Bakas et al. .......................... 502/66

Primary Examiner—Carl F. Dees
Attorney, Agent, or Firm—Thomas K. McBride; John F. Spears, Jr.; Hughes A. Blair

[57] ABSTRACT

Superior aromatic alkylation and transalkylation performance is obtained with a novel catalytic composition comprising a hydrogen form mordenite incorporated with alumina. The superior performance is a direct result of the catalyst composition having a surface area of at least 580 $m^2/g$. A novel method of preparing a catalyst having a surface area of at least 580 $m^2/g$ is characterized by contacting a formed catalytic composite with an acidic aqueous solution.

10 Claims, 1 Drawing Sheet

CATALYTIC COMPOSITION FOR THE ALKYLATION AND TRANSALKYLATION OF AROMATIC HYDROCARBONS

CROSS-REFERENCE TO RELATED APPLICATIONS

This application is a continuation-in-part of prior copending application Ser. No. 932,113 filed Nov. 18, 1986 now U.S. Pat. No. 4,735,924 which is a continuation-in-part of application Ser. No. 772,099 filed Sept. 3, 1985, now abandoned, the contents of which are incorporated herein by reference thereto.

BACKGROUND OF THE INVENTION

The present invention is related to an improved catalytic composition and an alkylation or transalkylation process embodying that catalytic composition. More particularly, this invention involves an alkylation or transalkylation catalyst composition comprising a hydrogen form crystalline aluminosilicate zeolite and a refractory inorganic oxide.

The alkylation or transalkylation of aromatics are processes well known for their ability to produce such monoalkylaromatic products as ethylbenzene, cumene, linear alkylbenzenes, and so forth. Such monoalkylaromatic compounds are important chemical precursors in the production of detergents and polymers among others. Alkylation catalysts that are known to produce alkylaromatic compounds include the well-known Friedel-Crafts catalysts: sulfuric acid, phosphoric acid, hydrofluoric acid, and aluminum chloride in either liquid or solid supported form. Solid granular catalysts such as clays, zeolites, and amorphous materials have also been utilized as alkylating reactants in both a modified and naturally occurring form.

A myriad of processing schemes employing an alkylation reaction zone and/or a transalkylation reaction zone are well known to produce monoalkylaromatic products in high yields. One drawback concerning existing alkylation/transalkylation processes is the potential for the alkylatio and/or the transalkylation catalyst to produce undesirable products such as alkylating agent oligomers, heavy polyaromatic compounds, and unwanted monoalkylaromatics. The alkylating agent oligomers can be especially troublesome as they are often recovered with the desired monoalkylaromatic product where they can detrimentally affect the utility of the monoalkylaromatic product in further conversion processes. An example of this would be the contamination of cumene with propylene oligomers which may reduce the utility of using such contaminated cumene as a phenol process feedstock and ultimately for the production of phenolic resins due to the presence of the oligomers as an inert compound within the cross-linked resins.

Another drawback inherent to some existing alkylation/transalkylation reaction zone containing processes is the use of Friedel-Crafts catalysts such as solid phosphoric acid or hydrofluoric acid as the alkylation and/or transalkylation catalyst. Many of these catalysts require a water cofeed and produce an extremely corrosive sludge by-product. The utilization of such sludge-producing catalysts in an alkylation process requires that special design considerations be made regarding unit metallurgy, safety, and by-product neutralization. Such design considerations are typically costly and may add significantly to the construction and operations costs of such processes. Additionally, the use of Friedel-Crafts catalyst requires a once-through processing scheme to ensure that damaging corrosive materials are not recycled into the reaction zone. This requirement necessitates the operation of the process at high conversion conditions which tend to produce greater amounts of unwanted by-products such as alkylating agent oligomers and heavy by-products.

More recently, crystalline aluminosilicate zeolites which have shown catalytic activity have been effectively used in the alkylation and transalkylation of aromatics. Both natural and synthetic crystalline aluminosilicates have been employed. Included among these are the Type X and Type Y zeolites as well as synthetic mordenite.

Specifically, the zeolites known as mordenites have received great attention. Mordenites are crystalline natural or synthetic zeolites of the aluminosilicate type; generally, they have a composition expressed in moles of oxide of

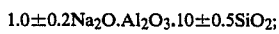

$$1.0\pm0.2Na_2O.Al_2O_3.10\pm0.5SiO_2;$$

the quantity of $SiO_2$ may also be larger. Instead of all or part of the sodium, other alkali metals and/or alkaline earth metals may be present.

In general, it has been found that the sodium form of mordenite is not particularly effective for the alkylation or transalkylation of hydrocarbons and that replacing all, or for the greater part, of the sodium cations with hydrogen ions yields the more advantageous hydrogen form mordenite. Conversion of the sodium form to the hydrogen form can be accomplished by a number of means. One method is the direct replacement of sodium ions with hydrogen ions using an acidified aqueous solution where the process of ion exchange is employed. Another method involves substitution of the sodium ions with ammonium ions followed by decomposition of the ammonium form using a high temperature oxidative treatment.

The activity and selectivity of alkylation or transalkylation catalysts depend on a variety of factors, such as the mode of catalyst preparation, the presence or absence of promoters, quality of raw materials, feedstock quality, process conditions, and the like. Suitable catalysts can be conventionally prepared by combining commercially available crystalline zeolites, such as, a hydrogen form mordenite, with a suitable matrix material. A new catalyst has now been discovered which exhibits greatly improved alkylation and transalkylation performance when compared to conventionally prepared catalysts.

OBJECTS AND EMBODIMENTS

Accordingly, there is provided a catalyst composition for the alkylation and transalkylation of aromatic hydrocarbons, which comprises a hydrogen form mordenite, and from about 5 to 25 wt.% alumina. The support is contacted with an acidic aqueous solution after it is formed. The acidic contacting occurs at conditions selected to increase the surface area of the composite at least 580 m²/g without increasing the silica/alumina ratio of the mordenite.

In another aspect, the invention is a method of manufacturing the aforementioned catalyst composition. Manufacturing of the catalyst comprises forming a composite comprising hydrogen form mordenite and from about 5 to 25 wt.% alumina, thereafter contacting formed composite with an acidic aqueous solution under conditions selected to increase the surface area of the composite at least 580 m²/g without increasing the silica/alumina ratio of the mordenite.

In another aspect, the invention is a process by alkylating or transalkylating an aromatic hydrocarbon by contacting a feedstock comprising an aromatic substrate and an alkylating agent or in the case of transalkylation with a transalkylatable aromatic hydrocarbon in a reaction zone with the catalyst composition described above.

These, as well as other embodiments of the present invention, will become evident from the following, more detailed description.

INFORMATION DISCLOSURE

The prior art recognizes a myriad of catalyst formulations for the alkylation or transalkylation of hydrocarbons. It is well known that acids, such as strong minerals acids, can be used to modify crystalline aluminosilicate zeolite powders through decationization and dealumination. Ammonium compounds have also been successfully employed to convert crystalline aluminosilicates from alkali and/or alkaline metal cation form to the hydrogen form. Combinations of zeolite and refractory inorganic oxide have been disclosed, however, the art is silent as to the inherent problem of loss of the zeolite surface area as result of dilution and forming techniques associated with the refractory inorganic oxide.

Combinations of the acid and ammonium treatments have been disclosed for use on aluminosilicate powders. U.S. Pat. Nos. 3,475,345 (Benesi) discloses a method of converting aluminosilicate zeolites, particularly a sodium form synthetic mordenite, to the hydrogen form utilizing a three-step pretreatment performed on the powdered zeolite. These pretreatment steps consist of: (1) a hot acid treatment, (2) a cold acid treatment, and (3) treatment with an ammonium compound. U.S. Pat. No. 3,442,794 (Van Helden et al) also discloses a method for the pretreatment of aluminosilicate zeolites to the hydrogen form. Again, the preferred zeolite is the synthetic sodium form of mordenite. The method disclosed is very similar to U.S. Pat. No. 3,475,345 mentioned above, with the distinguishing feature being a separately performed two-step pretreatment with (1) an acid compound and (2) an ammonium compound in arbitrary order. An important feature of both references is that the treatments are performed solely on the aluminosilicate zeolite with the express intention of modifying said zeolite before being utilized in a catalyst formulation and that no mention of the importance of the surface area of the catalytic composite is disclosed. This is distinguished from the present invention in that any treatment performed is subsequent to the zeolite being incorporated into a formed catalyst composite and more importantly without any apparent modification of the zeolite itself.

Treatment of the aluminosilicates with acid have not only been effective for conversion to the hydrogen form, but also have been used as a means for increasing the silica to alumina ratio. Typically, a silica to alumina ratio of about 10:1 is observed for a sodium form synthetic mordenite and is substantially unchanged if an ammonium treatment is used to convert the mordenite to the hydrogen form. If a mordenite powder is subjected to an acid treatment as taught in U.S. Pat. No. 3,597,155 (Flanigen), an increase in the silica to alumina ratio is effected. The acid treatment is believed to cause a reduction of the framework tetrahedra aluminum atoms, thus increasing the proportion of silicon atoms present in the zeolite structure.

Transalkylation performance is enhanced when the silica to alumina ratio of a mordenite powder is increased. U.S. Pat. No. 3,551,510 (Pollitzer et al) teaches the use of a hot hydrochloric acid extracted mordenite catalyst in a transalkylation reaction zone. Again, this reference specifically teaches of the use of acid treatment on the zeolite powder alone for the purpose of increasing the silica to alumina ratio, whereas the subject invention incorporates an already high silica to alumina ratio crystalline aluminosilicate into the catalytic composite and post-treats with acid to clean out the catalyst pores and thereby increase the surface area of the catalyst. These references also do not teach the importance of the surface area of the catalytic composite or its relationship to aromatic alkylation or transalkylation performance.

A common attribute of the above-mentioned prior art is that, in all cases, the crystalline aluminosilicate alone, in particular the synthetic sodium form of mordenite, is subjected to an acid and/or an ammonium pretreatment step(s) to modify the aluminosilicate before its incorporation into the catalyst composition. Although the pretreatment of mordenite as described in the above references enhances the performance of catalytic composites comprising such pretreated mordenite, further improvements are still obtainable.

BRIEF DESCRIPTION OF THE DRAWINGS

FIG. 1 is a graph of the diisopropylbenzene (DIPB) conversion in percent expressed alternatively as:

$$\left(1 - \frac{\text{(moles DIPB in feed)}}{\text{(moles DIPB in product)}}\right) \times 100$$

plotted against hours on-stream.

Figure 2:
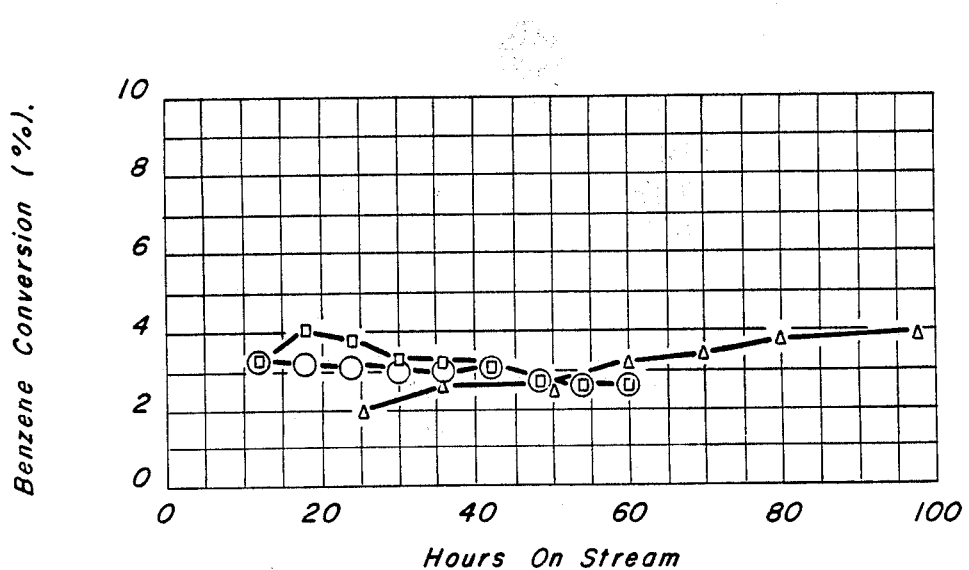

FIG. 2 is a plot of benzene conversion in percent plotted against hours on-stream where benzene conversion may be expressed as:

$$\left(1 - \frac{\text{(moles benzene in feed)}}{\text{(moles benzene in product)}}\right) \times 100.$$

DETAILED DESCRIPTION

While previous work dealt exclusively with pretreatment of the aluminosilicate component of a catalyst, it is one of the objects of the present invention to provide a novel catalyst composition which is characterized by exceptionally high surface area and which exhibits improved alkylation and transalkylation performance.

According to the present invention, there is provided a catalyst composition for the alkylation or transalkylation of aromatic hydrocarbons. The catalyst composition of the present invention comprises a hydrogen form mordenite and from about 0.5 to 50 wt.% alumina, and preferably 5 to 25 wt.% alumina with said catalyst composition having a surface area of at least 580 m²/g. We have found that significant improvements in alkylation and transalkylation performance are realized when the surface area of the catalyst composition is at or above 580 m²/g. Although a maximum surface area of the catalyst composition has not been determined experimentally, it is believed that an upper limit of 700 m²/g is possible. Obtaining such a high surface area in the range from about 580 to 700 m²/g is the object of one of the embodiments of the subject invention and is further illustrated in subsequent examples.

An essential component of the instant invention is the hydrogen form mordenite. While mordenite is naturally occurring, a variety of synthetic mordenites are available commercially, usually in a powder form. These synthetic mordenites can be obtained in both the sodium form and hydrogen form and at varied silica to alumina ratios. It is a preferred embodiment of the present invention that the mordenite be of the hydrogen form and that the silica to alumina ratio be at least 16:1, more specifically, in the range from 16:1 to 60:1. The pretreatment steps taught in the aforementioned references are routinely and typically employed in the manufacture of commercially available mordenite powders which meet the requirements as a starting material as set forth in the present invention. These pretreatment steps are used to increase the silica to alumina ratio of the mordenite zeolite and to convert the sodium form to the more desirable hydrogen form.

The hydrogen form mordenite is incorporated with alumina and formed into a catalytic composite. The formed catalytic composite may be prepared by an known method in the art including the well-known oil drop and extrusion methods. The hydrogen form mordenite may be present in an amount within the range of 50 to about 99.5 wt.% preferably within the commercially desirable range of 75 to about 95wt.%. Thus, the alumina is preferably present in an amount within the range of from about 5 to about 25 wt.% based on total weight of the catalyst composition.

The preferred alumina for use in the present invention is selected from the group consisting of gamma-alumina, eta-alumina, and mixtures thereof. Most preferred is gamma-alumina. Other refractory inorganic oxides which may be used include, for example, silica gel, silica-alumina, magnesia-alumina, zirconia alumina, phosphorus-containing alumina, and the like.

Surprisingly, and unexpectedly, it has been found that a catalyst composition prepared in accordance with and containing the components as claimed in the invention will possess a surface area higher than any catalyst heretofore described in the art. This high surface area of at least 580 m²/g is surprising when one considers not only the diluting affect of an alumina support material having relatively low surface area (maximum approximately 250 m²/g), but also considering the lowering of surface area caused by the particular forming technique employed. As exemplified herein below, catalyst of the prior art do not obtain the high surface area of the instant catalyst and thus demonstrate inferior performance, particularly as alkylation and transalkylation catalysts. The prior art does not teach or suggest how to obtain a mordenite/alumina catalyst having a surface area of at least 580 m²/g. Surface area, as referred to herein, is determined by employing the Langmuir method of correlating adsorption/desorption isotherm data. The Langmuir method is especially suitable for catalytic composites containing high percentages of crystalline aluminosilicates. The data needed for the Langmuir method is typically obtained by well known absorption/desorption apparatuses, preferably a nitrogen adsorption/desorption apparatus. Therefore, the present invention allows for a catalyst composition using a high surface area mordenite without loss of this surface area when formed with alumina to give a commercially acceptable formulation. Likewise, the benefit of the presence of alumina, which imparts, among other things, strength to the catalyst composition, may be achieved without penalty with regard to the surface area of the mordenite.

Any method may be employed which results in a final catalyst composite having at least a surface area of 580 m²/g. Catalyst compositions with high surface areas can be arrived at in a number of ways, such as, using a hydrogen form mordenite powder which inherently has a very high surface area, or by having one component of the composite, which has a high surface area, in great proportion to other components. A preferred method of achieving a surface area of at least 580 m²/g is to contact the formed catalytic composite with an acidic aqueous solution. This acidic aqueous solution may contain ammonium ions. The formed catalyst composite may be dried and/or calcined prior to its contact with the aqueous solution.

The acidic nature of the aqueous solution is attained by employing an acid. Particularly suitable are strong mineral acids such as $H_3PO_4$, $H_2SO_4$, $HNO_3$, and HCl. HCl is the preferred acid of the present invention. Of course, it is contemplated that mixtures of various acids may also be employed. If the acidic aqueous solution contains ammonium ions, the preferred source of these ions is $NH_4Cl$, but any ammonium compound which can form ammonium ions, such as $NH_4OH$, $NH_4NO_3$, $NH_4$ sulfates, $NH_4$ phosphates and the like, should be suitable.

Concentrations of the acid and ammonium ions in the aqueous solution are not critical and can vary from 0.5M to 6M for the acid concentration and 0.5M to 4M for the ammonium ion concentration. Particularly good results are obtained using a solution containing acid and ammonium ion concentrations within the range of 2 to 5M for the acid and 1 to 3M for the ammonium ion.

A plurality of methods for contacting the formed catalytic composite and the acidic aqueous solution is envisioned with no one method of particular advantage. Such contacting methods may include, for example, a stationary catalyst bed in a static solution, a stationary catalyst bed in an agitated solution, a stationary catalyst bed in a continuously flowing solution, or any other means which efficiently contacts the catalyst composition with the acidic aqueous solution.

The temperature of the contacting solution should be within the range of 25° C. to about 100° C., preferably within the range of from about 50° C. to about 98° C. The time required for the contacting step will depend upon concentrations, temperature and contacting efficiency. In general, the contacting time should be at least 0.5 hour, but not more than 4 hours, preferably between 1 and 3 hours in duration.

As a result of contacting the formed catalytic composite with the acidic aqueous solution, an increase in the measured surface area is observed. Surprisingly and unexpectedly, this increase in surface area, to 580 m²/g or higher, is not accompanied by an increase in the silica to alumina ratio of the hydrogen form crystalline aluminosilicate as measured by Magic Angle Spinning NMR (MASNMR). The MASNMR technique, which is a well known analytical method of the art, indicates no reduction in the framework tetrahedral aluminum atoms of catalyst compositions of the present invention.

Although it is not certain the exact reason why the surface area is higher after contacting the formed catalytic composite, it is believed that the acidic aqueous solution is removing occluded ions from the mordenite which are deposited therein as a result of the forming technique employed.

The catalyst of the instant invention has particular utility in the alkylation or transalkylation of aromatic hydrocarbons.

In the alkylation of an aromatic substrate with an alkylating agent in a process utilizing the catalyst composition of this invention, the alkylating agent which may be charged to the alkylation reaction zone may be selected from a group of diverse materials including monoolefins, diolefins, polyolefins, acetylenic hydrocarbons, and also alkylhalides, alcohols, ethers, esters, the later including the alkysulfates, alkylphosphates and various esters of carboxylic acids. The preferred olefin-acting compounds are olefinic hydrocarbons which comprise monoolefins containing one double bond per molecule. Monoolefins which may be utilized as olefin-acting compounds in the process of the present invention are either normally gaseous or normally liquid and include ethylene, propylene, 1-butene, 2-butene, isobutylene, and the higher molecular weight normally liquid olefins such as the various pentenes, hexenes, heptenes, ocetenes, and mixtures thereof, and still higher molcular weight liquid olefins, the latter including various olefin polymers having from about 9 to about 18 carbon atoms per molecule including propylene trimer, propylene tetramer, propylene pentamer, etc. $C_9$-$C_{18}$ normal olefins may be used as may cycloolefins such as cyclopentene, methylcyclopentene, cyclohexene, methylcyclohexene, etc. may also be utilized, although not necessarily with equivalent results.

It is a preferred embodiment of the present invention that the monoolefin contains at least 2 and not more than 14 carbon atoms. More specifically, it is preferred that the monoolefin is propylene.

The aromatic substrate component of the alkylation process of this invention which is charged to the alkylation reaction zone in admixture with the alkylating agent may be selected from a group of aromatic compounds which include individually and in admixture with benzene and monocyclic alkyl-substituted benzene having the structure:

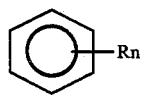

where R is a hydrocarbon containing 1 to 14 carbon atoms, and n is an integer from 1 to 5. In other words, the aromatic substrate portion of the feedstock may be benzene, benzene containing from 1 to 5 methyl and/or ethyl group substituents, and mixtures thereof. Non-limiting examples of such feedstock compounds include benzene, toluene, xylene, ethylbenzene, mesitylene (1,3,5-trimethylbenzene), cumene, n-propylbenzene, butylbenzene, dodecylbenzene, tetradecylbenzene, and mixtures thereof. It is specifically preferred that the aromatic substrate is benzene.

In a continuous process for alkylating aromatic hydrocarbons with olefins, the previously described reactants are continuously fed into a pressure vessel containing the above-described catalyst. The feed admixture may be introduced into the alkylation reaction zone containing the alkylation catalyst at a constant rate, or alternatively, at a variable rate. Normally, the aromatic substrate and olefinic alkylating agent are contacted at a molar ratio of from about 1:1 to 20:1 and preferably from about 2:1 to 8:1. The preferred molar feed ratios help to maximize the catalyst life cycle by minimizing the deactivation of the catalyst by coke and heavy material deposition upon the catalyst. The catalyst may be contained in one bed within a reactor vessel or divided up among a plurality of beds within a reactor. The alkylation reaction system may contain one or more reaction vessels in series. The feed to the reaction zone can flow vertically upwards, or downwards through the catalyst bed in a typical plug flow reactor, or horizontally across the catalyst bed in a radial flow type reactor.

Temperatures which are suitable for use in the alkylation process herein are those temperatures which initiate a reaction between an aromatic substrate and the particular olefin used to selectively produce the desired product. Generally, temperatures suitable for use are from about 100° to about 390° C., especially from about 150° to about 275° C. Pressures which are suitable for use herein preferably are above about 1 atmosphere but should not be in excess of about 130 atmospheres. An especially desirable pressure range is from about 10 to about 40 atmospheres; with a liquid hourly space velocity (LHSV) based upon the aromatic substrate feed rate of from about 0.5 to about 50 $hr^{-1}$, and especially from about 2 to about 10 $hr^{-1}$. It should be noted that the temperature and pressure combination used herein is to be such that the alkylation reaction takes place in essentially the liquid phase. In a liquid phase process for producing alkylated aromatics, the catalyst is continuously washed with reactants, thus preventing buildup of coke precursors on the catalyst. This results in reduced amounts of carbon forming on said catalyst in which case catalyst cycle life is intended as compared to a gas phase alkylation process in which coke formation and catalyst deactivation is a major problem. To further reduce the rate of catalyst deactivation, it is contemplated that $H_2$ may be added to the alkylation reaction zone feed in an amount sufficient to saturate the respective reaction zone liquid feed. The addition of $H_2$ in equilibrium amounts to the respective liquid phase feed streams helps to reduce the catalyst deactivation rate by inhibiting the polymerization potential of pore blocking polymerizable compounds produced by the process.

The products of the alkylation reaction or transalkylation reaction as hereinbelow described may be recovered using techniques known in the prior art. Examples of some of the separation techniques that could be employed alone or in combination to recover alkylation reaction zone products are: distillation including vacuum, atmospheric, and superatmospheric distillation; extraction techniques including, for example, liquid/liquid extractions, vapor/liquid extractions, supercritical extractions and others; absorption techniques, adsorption techniques, and any other known mass transfer techniques which can achieve the recovery of the desired separation zone products in essentially pure fractions. The separation processes mentioned above are included as examples of the many techniques which could be utilized to achieve the necessary separation, purification, and recovery of the alkylation reaction zone products. Hence, separation zone processing conditions are not disclosed as they will depend upon the choice of the separation techniques employed and further upon the reactants used and the configuration of the separation zone equipment. It is expected that continuous distillation will be the primary separation technique used. The optimal distillation conditions will again depend upon the exact scheme chosen to achieve the desired separation.

The catalyst of this invention is also useful in the transalkylation of transalkylatable aromatics. The transalkylation process of this invention preferably accepts as feed a transalkylatable hydrocarbon in conjunction with an aromatic substrate. The transalkylatable hydrocarbons useful in the transalkylation process are comprised of aromatic compounds which are characterized as constituting an aromatic substrate based molecule with one or more alkylating agent compounds taking the place of one or more hydrogen atoms around the aromatic substrate ring structure. The alkylating agent compounds identified above are identical to those described as useful in the alkylation process above and preferably $C_2$–$C_{14}$ aliphatic hydrocarbons.

The aromatic substrate useful as a portion of the feed to the transalkylation process is the same as that described above as useful in the alkylation process employing the instant catalyst.

The transalkylation process of this invention may have a number of purposes. In one, the catalyst of the transalkylation reaction zone is utilized to remove the alkylating agent compounds in excess of one from the ring structure of polyalkylated aromatic compounds and to transfer the alkylating agent compound to an aromatic substrate molecule that has not been previously alkylated, thus increasing the amount of the desired aromatic compounds produced by the process. In a related purpose, the reaction performed in the transalkylation reaction zone involves the removal of all alkylating agent components from a substituted aromatic compound and in doing so, converting the aromatic substrate into benzene.

To transalkylate polyalkylaromatics with an aromatic substrate, a feed mixture containing an aromatic substrate and polyalkylated aromatic compounds in mole ratios ranging from 1:1 to 50:1 and preferably from 4:1 to 10:1 are continuously or intermittently introduced into a transalkylation reaction zone containing the catalyst of this invention at transalkylation conditions including a temperature from about 100° to about 390° C., and especially from about 125° to about 275° C. Pressures which are suitable for use herein preferably are above 1 atmosphere but should not be in excess of about 130 atmospheres. An especially desirable pressure range is from about 10 to about 40 atmospheres. A liquid hourly space velocity (LHSV) of from about 0.1 to about 50 hr$^{-1}$, and especially from about 0.5 to about 5 hr$^{-1}$ based upon the combined aromatic substrate and polyalkylaromatic feed rate is desirable. While the process of the instant invention may be performed in the vapor phase, it should be noted that the temperature and pressure combination utilized in the transalkylation reaction zone is preferred to be such that the transalkylation reactions take place in essentially the liquid phase. In a liquid phase transalkylation process for producing monoalkylaromatics, the catalyst is continuously washed with reactants, thus preventing buildup of coke precursors on the catalyst. This results in reduced amounts of carbon forming on said catalyst in which case catalyst cycle life is extended as compared to a gas phase transalkylation process in which coke formation and catalyst deactivation is a major problem. Additionally, the selectivity to monoalkylaromatic production, especially cumene production, is higher in the catalytic liquid phase transalkylation reaction herein as compared to catalytic gas phase transalkylation reaction.

The following examples are presented for purposes of illustration only and are not intended to limit the scope of the present invention.

EXAMPLES

A number of experiments were conducted to study how changes in the surface area of alkylation or transalkylation catalyst composites affect process performance. Three catalysts were prepared for evaluation. In all the catalyst preparations described in the following examples, the starting material was the hydrogen form, low sodium, partially dealuminated synthetic mordenite powder (marketed by Union Carbide under the name LZ-M-8), hereinafter referred to as the as-received mordenite.

EXAMPLE I

Experiments were undertaken to study the performance of two catalytic composites in promoting alkylation and transalkylation reactions.

Catalyst A was formulated by a method inconsistent with that of the alkylation or transalkylation catalyst of the present invention. The as-received mordenite powder was mixed with an alumina powder to a weight ratio of 9:1, followed by the addition of an acidified peptization solution. The admixture was then extruded by means known in the art. After the extrusion process, the extrudate was dried and calcined. The resulting surface area of this catalyst was 540 m$^2$/g.

EXAMPLE II

The catalyst base formulation used for Catalyst B is identical to that used for Catalyst A of Example I. The difference arises in the steps following the drying and calcination of the acid peptized silica/mordenite extrudate. Following the drying and calcination steps, the extrudate was exposed to an aqueous solution comprising 10 wt.% HCl and 10 wt.% NH$_4$Cl at 60° C. for 150 minutes at a solution to zeolite volumetric ratio of 5:1. After the acid wash step, the catalyst was again dried and calcined. Catalyst B is the acid-washed catalyst of the present invention. The resulting surface area of this catalyst was 620 m$^2$/g.

EXAMPLE III

Catalyst C was formulated by a method inconsistent with that of the catalyst of the present invention. To prepare Catalyst C, a mixture of 50 wt.% mordenite powder and 50 wt.% alumina powder was combined with a 5.5 wt.% nitric acid solution. The resulting dough was extruded by means known in the art. The extrudate was calcined at 150° C. for 1 hour and then at 480° C. for 3 hours. The calcined extrudate was next contacted with a 15 wt.% solution of ammonia for 1 hour and then dried. The dried, finished extrudate was calcined at 150° C. for 1 hour and 480° C. for 2 hours. The finished catalyst had a surface area of 450 m$^2$/g.

EXAMPLE IV

Catalysts B and C as described in the previous examples were evaluated for aromatic alkylation performance in a flow-through reactor containing 20 cc of catalyst by processing a feed comprising a mixture of benzene and propylene at a 4:1 molar ratio. Conventional product recovery and analysis techniques were used to evaluate the catalyst performance in each case.

The operating conditions used to evaluate the alkylation performance of the three catalysts comprised a reactor pressure of 34 atmospheres, a liquid hourly space velocity of 4 hr$^{-1}$ based upon the benzene feed rate, and a maximum temperature of 200° C. No recycle of the reactor effluent to the reactor inlet was employed in this testing. The results of the pilot plant tests can be found in Table 1 below.

TABLE 1

| | Alkylation Reaction Selectivities | |
|---|---|---|
| Yields (mole %) | Catalyst B 200° C. | Catalyst C 200° C. |
| Cumene | 85.9 | 82.6 |
| Diisopropylbenzenes | 12.2 | 16.1 |
| para | 4.4 | 5.9 |
| meta | 7.7 | 10.2 |
| ortho | 0.1 | — |

The pilot plant tests indicate that Catalyst B, the alkylation catalyst of the present invention produces an alkylation product which comprises 98.1 mole % isopropylbenzene compounds of which 85.9 wt.% is the monoalkylaromatic cumene. Catalyst C, the low mordenite/low surface area catalyst of the prior art produces an alkylate with 82.6 mole % of the monoalkylaromatic cumene. The only difference in preparation of the two catalysts was that Catalyst B of the instant invention was treated with acid after forming which resulted in an increase in the surface area of the catalyst.

Thus, it can be concluded that the catalyst of the instant invention is more useful in the production of monoalkylaromatics in an aromatic alkylation process directed toward the production of such products than the non-acid washed catalyst of the prior art.

EXAMPLE V

Figure 1:
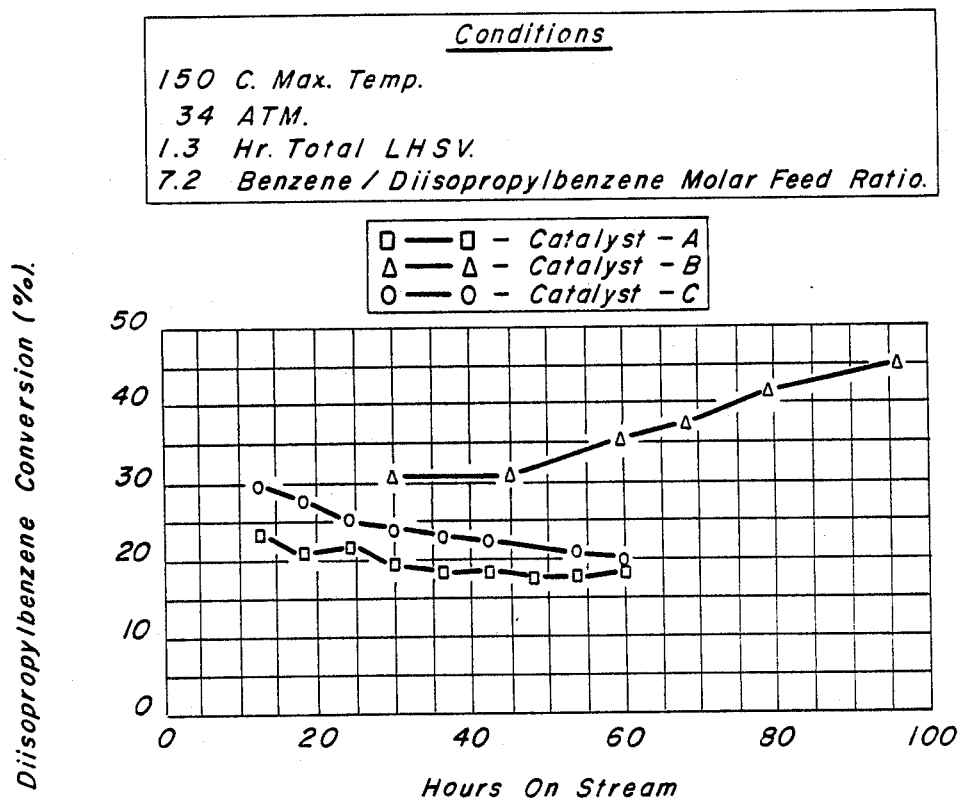

Catalyst B, the transalkylation catalyst of the present invention, was tested at transalkylation reaction conditions along with Catalyst A, a non-acid washed mordenite catalyst, and Catalyst C, a low surface area mordenite catalyst, both not catalysts of the present invention. The catalysts were evaluated in a pilot plant consisting of a tubular reactor holding 50 cc of transalkylation catalyst and a product recovery zone. To the reactor was fed a liquid feed blend comprised of 7.2 moles of benzene, 1 mole of diisopropylbenzene, and 0.25 moles of other alkybenzenes at a total liquid hourly space velocity (LHSV) of 1.3 hr$^{-1}$. The reactor pressure was operated at 34 atmospheres, and the reaction temperature was held at 150° C. maximum. The results of the pilot plant tests are presented in FIGS. 1 and 2. It is evident from FIG. 1 that the diisopropylbenzene conversion capability of Catalyst B, the transalkylation catalyst of the instant invention, is much higher than that of the two catalysts not of the instant invention. The ability of all three catalysts to promote the reaction of benzene with polyalkylated aromatics as seen in FIG. 2 is similar in all cases. This leads to the conclusion that Catalyst B, the acid-washed high surface area transalkylation catalyst of the instant invention, is more efficient in the transalkylation of diisopropylbenzene with benzene to produce cumene at a high diisopropylbenzene conversion than a non-acid washed or low surface area mordenite containing catalyst. This is evidenced as mentioned by the ability of Catalyst B to utilize an amount of benzene similar to Catalysts A and C to produce a greater amount of isopropyl benzenes.

What is claimed is:

1. A catalytic composite comprising a hydrogen form mordenite dispersed in an alumina matrix, said composite containing from about 5 to 25 percent by weight of alumina and wherein said composite is contacted with an acidic aqueous solution after it is formed, said contacting occurring at conditions selected to increase the surface area of the composite to at least 580 m$^2$/g without increasing the silica/alumina ratio of the mordenite.

2. The catalytic composite of claim 1 wherein said composite is spherical, cylindrical, and/or granular in shape.

3. The catalytic composite of claim 1 wherein said alumina is selected from the group consisting of gamma-alumina, eta-alumina, and mixtures thereof.

4. The catalytic composite of claim 3 wherein said alumina is gamma-alumina.

5. The catalytic composite of claim 1 wherein the hydrogen form mordenite has a silica to alumina ratio of at least 16:1.

6. A method of manufacturing a catalytic composite comprising a hydrogen form mordenite dispersed in an alumina matrix, said composite comprising from about 5 to 25 percent by weight of alumina, said method comprising forming said support, and contacting said formed support with an acidic aqueous solution under conditions selected to increase the surface area of the composite to at least 580 m$^2$/g without increasing the silica/alumina ratio of the mordenite.

7. The catalytic composite of claim 6 wherein said composite is spherical, cylindrical, and/or granular in shape.

8. The catalytic composite of claim 6 wherein said alumina is selected from the group consisting of gamma-alumina, eta-alumina, and mixtures thereof.

9. The catalytic composite of claim 6 wherein said alumina is gamma-alumina.

10. The catalytic composite of claim 6 wherein the hydrogen form mordenite has a silica to alumina ratio of at least 16:1.

* * * * *